United States Patent [19]
Cadell et al.

[11] Patent Number: 5,429,128
[45] Date of Patent: Jul. 4, 1995

[54] FINGER RECEPTOR

[75] Inventors: Theodore E. Cadell; Donald B. MacHattie, both of Waterloo, Canada

[73] Assignee: CME Telemetrix Inc., Waterloo, Canada

[21] Appl. No.: 43,464

[22] Filed: Feb. 24, 1993

[51] Int. Cl.⁶ ............................................. A61B 5/00
[52] U.S. Cl. ................................................. 128/633
[58] Field of Search ............... 128/632, 633, 637, 665, 128/667, 687, 689

[56] References Cited

U.S. PATENT DOCUMENTS

| | | | |
|---|---|---|---|
| 3,463,142 | 8/1969 | Harte | 128/633 |
| 4,825,872 | 5/1989 | Tan et al. | 128/633 |
| 4,846,189 | 7/1989 | Sun | 128/667 |
| 4,913,150 | 4/1990 | Cheang et al. | 128/633 |
| 5,077,476 | 12/1991 | Rosenthal | 128/633 |
| 5,218,966 | 6/1993 | Yamasawa | 128/667 |

*Primary Examiner*—Lee S. Cohen
*Assistant Examiner*—Brian M. Green
*Attorney, Agent, or Firm*—Daryl W. Schnurr

[57] ABSTRACT

A finger receptor is used with a non-invasive monitoring device to determine non-invasively the concentration of known constituents in blood or tissue. The receptor has a channel for receiving a finger of a user. The channel has a light entrance and a light exit so that light can be passed from a light source through a finger located in the channel in a direction generally normal to the finger. Extraneous light is excluded and the finger is held in position by a spring-mounted roller. The receptor has sensing means to determine when a finger has been properly positioned in the channel. Previous devices are not capable of achieving repeatable results to a sufficient degree to replace invasive methods of testing.

23 Claims, 6 Drawing Sheets exit;

FINGER RECEPTOR

BACKGROUND OF THE INVENTION

1. Field of the Invention

This invention relates to a finger receptor for use with a non-invasive monitoring device for determining concentrations of various components of blood.

2. Description of the Prior Art

It is known to have a finger receptor having an oblong shape for receiving a finger. However, previous receptors are not sufficiently efficient to obtain accurate and consistent results for various types of users of the device.

Further, previous devices produce fluctuating results due to one or more of extraneous light, pulse rate, movement of the finger during testing, varying path lengths, various sizes of fingers, insufficient blood concentration within the finger and various colours of fingers.

SUMMARY OF THE INVENTION

A finger receptor, to receive a finger of a user, for use with a non-invasive monitoring device, is used with a light source. The receptor has a base containing an elongated channel sized to receive a finger, said channel having an opening to receive said finger and two sides with a light path entrance on one side and a light path exit on another side. The entrance and exit are sized and located so that at least some of the light passing through said entrance is received at said exit. The channel is shaped so that a finger properly inserted into said channel completely fills a zone of said channel located between said entrance and said exit so that no light from said entrance can reach said exit without passing through said finger. Light from the light source forms an optical path from said entrance to said exit with sensing means to determine when said finger is properly positioned in said channel.

DESCRIPTION OF A PREFERRED EMBODIMENT

Figure 1:
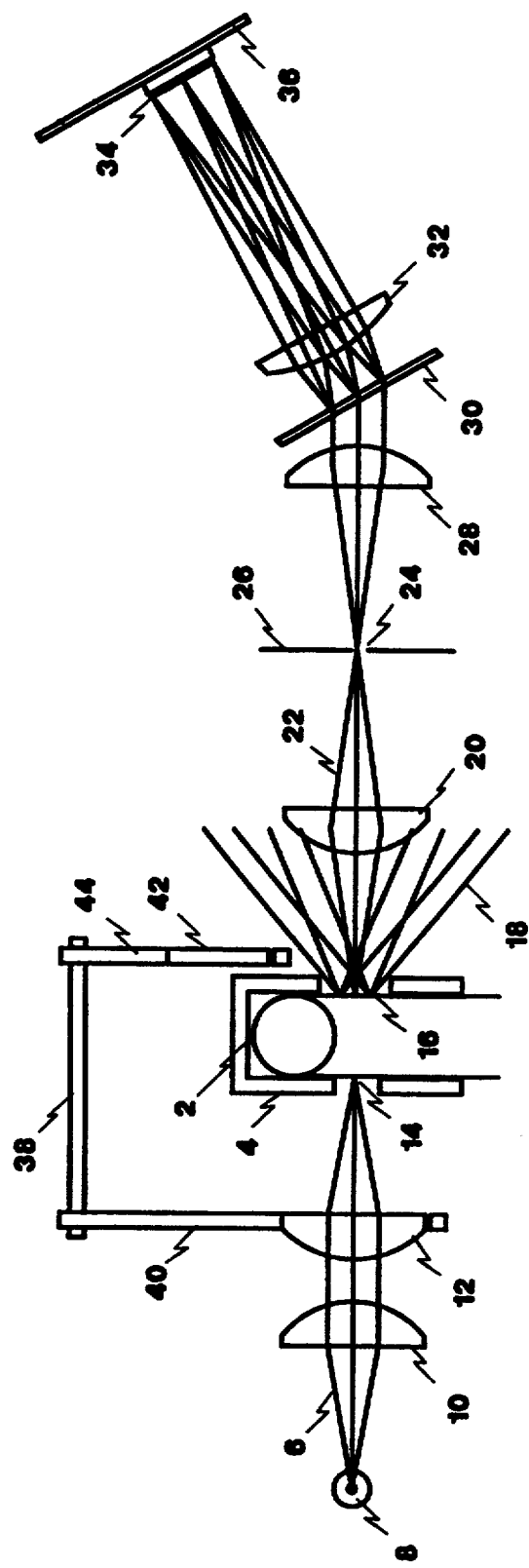
FIG. 1 is a schematic view of an optical system where a receptor is used with a non-invasive measurement device.

In FIG. 1, a finger 2 is located in a receptor 4. Light 6 from a light source 8, preferably a polychromatic light source, passes through a collimating lens 10 and then through a scanning focussing lens 12 into a light path entrance 14 in the receptor 4. The light 6 passes through the finger 2 and leaves the receptor 4 through light path exit 16. The scanning focussing lens 12 focuses the light 6 on the entrance 14. Light 18 from the exit 16 is diffused and scattered and some of the light 18 falls onto a focussing lens 20. That light 22, that falls on the lens 20, is focussed onto a slit 24 in a partition 26. From the slit 24, the light 22 passes through a collimating lens 28 and onto a grating 30. From the grating 30, the light 22 passes through a sensor focussing lens 32, which focusses the light onto a linear photo diode array 34. The array 34 is connected to a printed circuit board 36 for processing of data obtained from the differences in light intensity as the light passes through the finger.

The non-invasive monitoring device is not discussed in detail as the invention being claimed is the receptor. The receptor can be used with various non-invasive monitoring devices, one of which is described in detail in U.S. application Ser. No. 07/362,342 filed June 7th, 1989.

The scanning focussing lens 12 is mounted on a shaft 38 by means of an armature 40. The shaft 38 is rotatable about its longitudinal axis in either direction by operation of a motor (not shown in FIG. 1) so that the lens 40 may be moved into and out of the light path for finger and reference measurements respectively. While a finger is in the receptor 4, lens 12 is moved into the optical path and a scanning motor (not shown in FIG. 1) moves lens 12 back and forth relative to the entrance 14. A neutral density filter 42 is mounted on a support 44 to the same arm 38. When it is desired to take a reference measurement with the monitoring device, there is no finger in the receptor and the motor (not shown in FIG. 1) rotates the shaft 38 to move the filter 42 so that it is in line with the exit 16 and to move the lens 12 away from the entrance 14.

Figure 2:
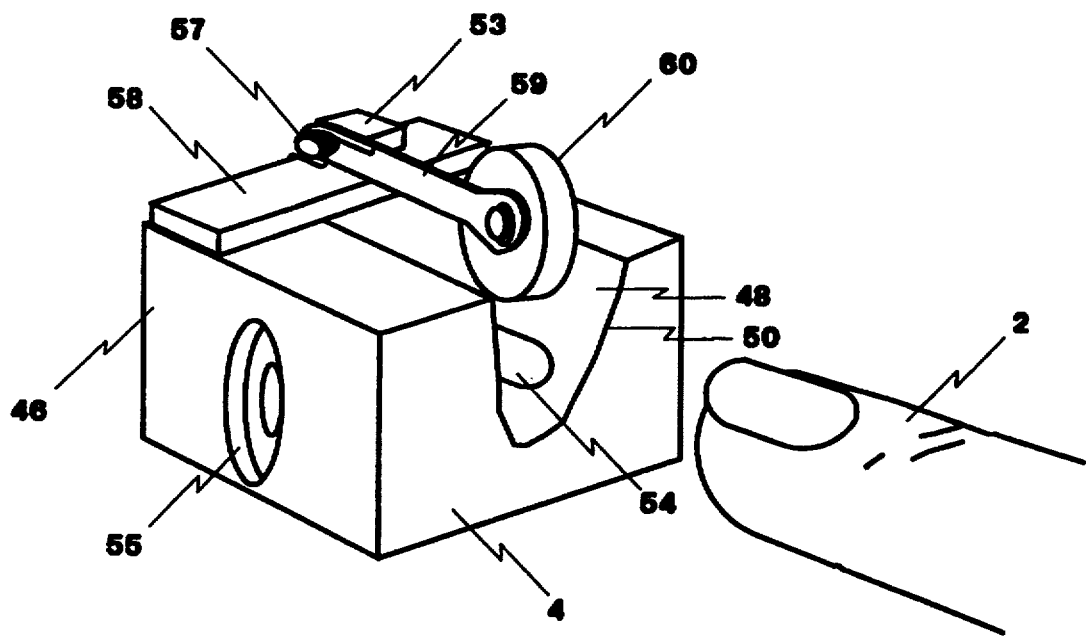
FIG. 2 is a perspective view of one embodiment of a receptor.
Figure 3:
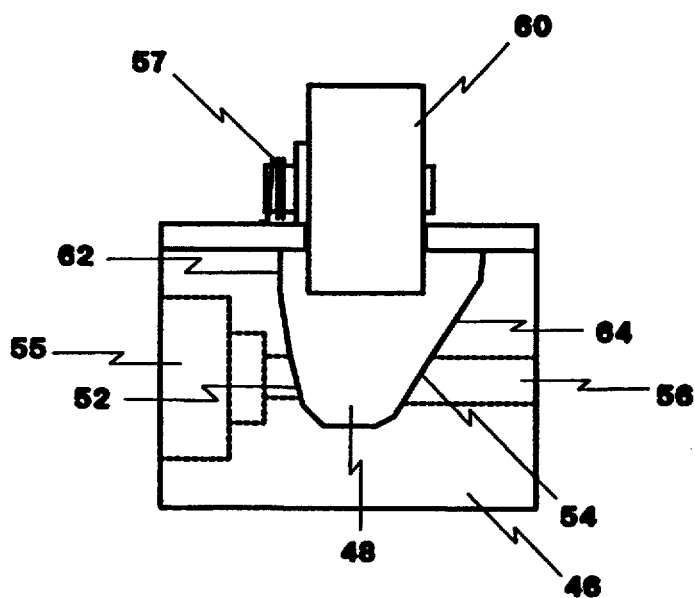
FIG. 3 is a front view of the receptor of FIG. 2.

In FIGS. 2 and 3, there is shown a perspective view and a sectional view of part of the receptor 4. The receptor 4 has a base 46 containing an elongated channel 48 shaped to receive the finger 2. The channel has a mouth 50 and has two sides with a light path entrance 52 on one side and a light path exit 54 on another side. The entrance 52 and the exit 54 are sized and located so that at least some of the light passing through said entrance is received at said exit. The entrance 52 is circular and the exit 54 has an oblong shape with a long side being in a direction parallel to the finger so that said exit can receive an increased amount of the light that has passed through said entrance. An entrance passage 55 has a circular cross-section that converges towards the channel 48. An exit passage 56 extends from the exit 54 and has parallel sides.

A torsion spring 57 has one end supported by a bar 58 and the other end of the spring is hooked over armature 59. The torsion spring is wrapped around a small axle supported by a small block 53. The armature 59 supports a roller 60 that is rotatably mounted thereon. The spring 57 provides a constant pressure on the finger of users within a particular size range. The roller 60 is oriented and located so that it rolls along the finger 2 as the finger is inserted longitudinally into the channel 48.

The roller applies light pressure to the finger to force the finger against the bottom of the channel. Also, the pressure applied by the roller causes blood within the finger to fill that tissue of the finger overlying the entrance and exit, thereby increasing the amount of blood in that part of the finger being monitored.

In FIG. 3, it can be seen that the channel 48 has one side 62 that is relatively steep and another side 64 that has a gentle slope. The steep side 62 allows light entering through the entrance 52 to intersect the finger at an angle that is close to 90°. It is desirable to have the entrance 52 as close to 90° to the light path as possible as this maximizes absorbtion and minimizes reflection of light by the surface of the body part. The gently sloping side 64 allows the channel to better accommodate fingers of different sizes. It can be seen that the entrance passage 55 has a tapered shape with the entrance passage converging as it approaches the side wall 62. The exit passage 56 extends from the side 64 but does not diverge or converge.

Figure 4:
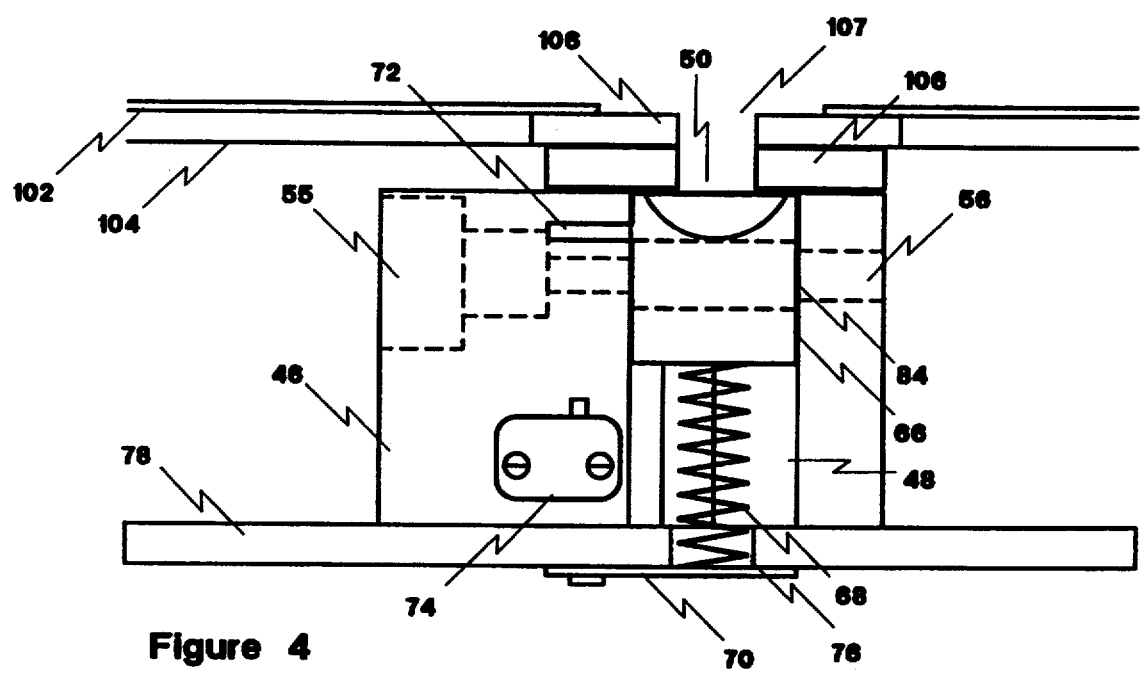
FIG. 4 is a top view of a receptor with a plunger in a rest position.
Figure 5:
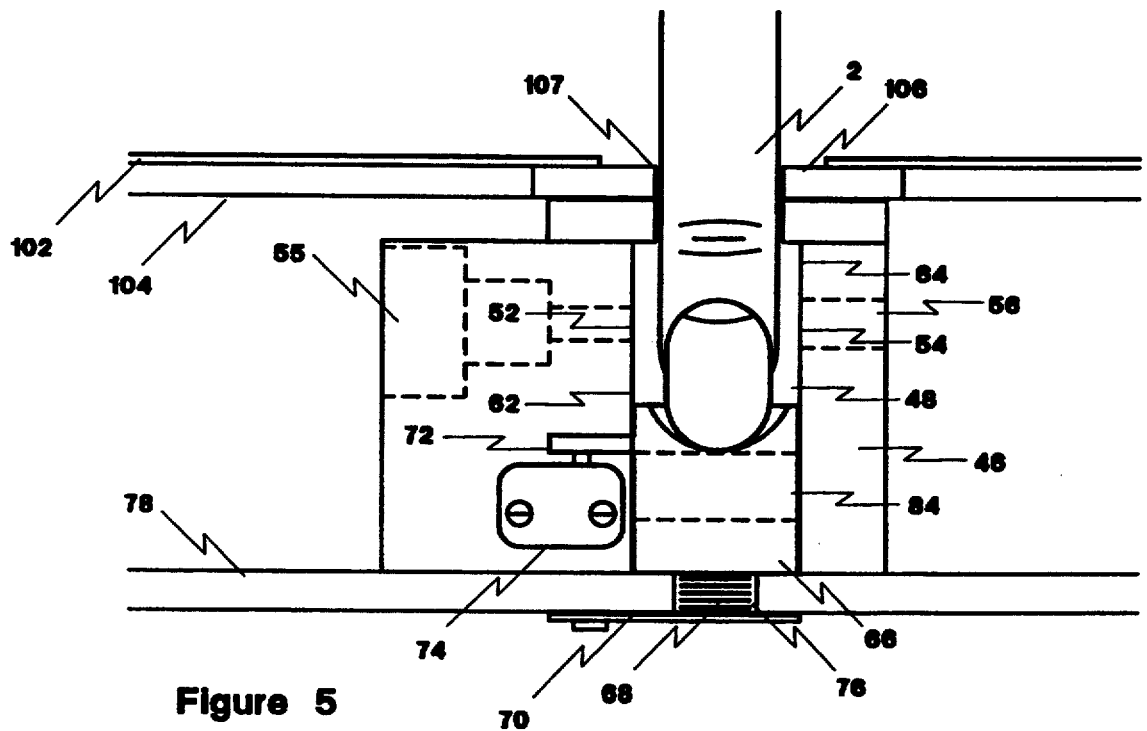
FIG. 5 is a top view of the receptor with a finger inserted in a channel and the plunger depressed.

In FIGS. 4 and 5, the roller and torsion spring have been deleted to expose a plunger 66 that is slidably mounted in the channel 48. A spring 68 is located between the plunger 66 and a plate 70 mounted across an inner end of the channel 48. The spring 68 forces the plunger outward to the mouth 50 when the plunger is in a rest position as shown in FIG. 4.

In FIG. 5, when a finger 2 has been inserted into the channel 48 through the mouth 50, the plunger 66 is pushed inward so that the spring 68 is compressed and a projection 72 on the plunger 66 triggers a micro-switch 74 mounted on a top of the base 46. The switch 74 is connected to activate the non-invasive monitoring device and to take measurements of variations in light intensity by activating the light source and having the light pass through the finger 2. Software monitoring of the micro-switch during the taking of measurements ensures that the switch is closed and that the finger is not removed. The spring 68 is located in an opening 76 within a support plate 78 across an inner end of the channel 48.

Surrounding the mouth 50 of the channel 48 is a foam plastic collar 106 that contains an aperture 107. The aperture 107 is aligned with the channel 48 so that when a finger is inserted through the aperture, the collar forms a seal around the finger to prevent outside light from entering the channel. A shield 104 prevents outside light from entering the area of the light source. Further, a platform 102 is a rectangular plate that is located to support a hand of the user when the finger is inserted into the channel. The platform 102 is located at an angle of 90° relative to the channel but could be mounted to be located at a lesser angle, for example 30°.

The entrance passage 55 (shown by dotted lines) is stepped down to converge at the side 62. An exit passage 56 has parallel sides that are much further apart in the horizontal direction than the sides of the entrance 52 at the wall 62. The actual intersection of the entrance 52 and the exit 54 is not shown in FIG. 5 as these intersections are covered by the finger 2. The plunger 66 has an opening 84 (shown by dotted lines) therein to connect the entrance 52 with the exit 54 when the plunger is in a rest position as shown in FIG. 4. In this manner, when the monitoring device is calibrated using the neutral density filter 42 shown in FIG. 1, light can be passed from the light source through the entrance passage 55, through the plunger 66 and out the exit 54 and exit passage 56 into the neutral density filter (not shown in FIGS. 4 and 5). The plunger 66 has a cutaway portion to accommodate the fingernail of the user.

Figure 6:
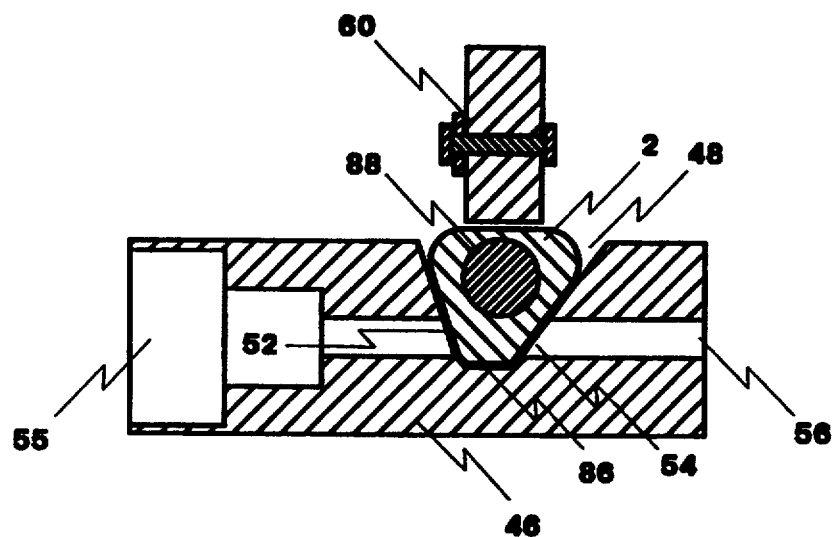
FIG. 6 is a sectional view across the channel of the device.
Figure 7:
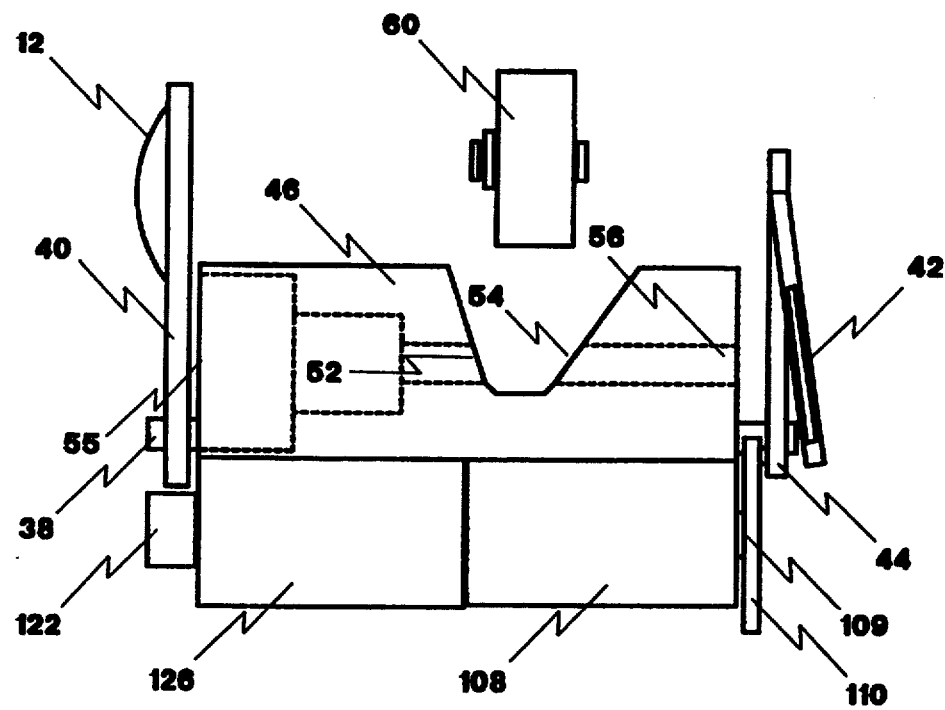
FIG. 7 is a front view of the receptor with the channel empty and a neutral density filter across a light path exit.
Figure 8:
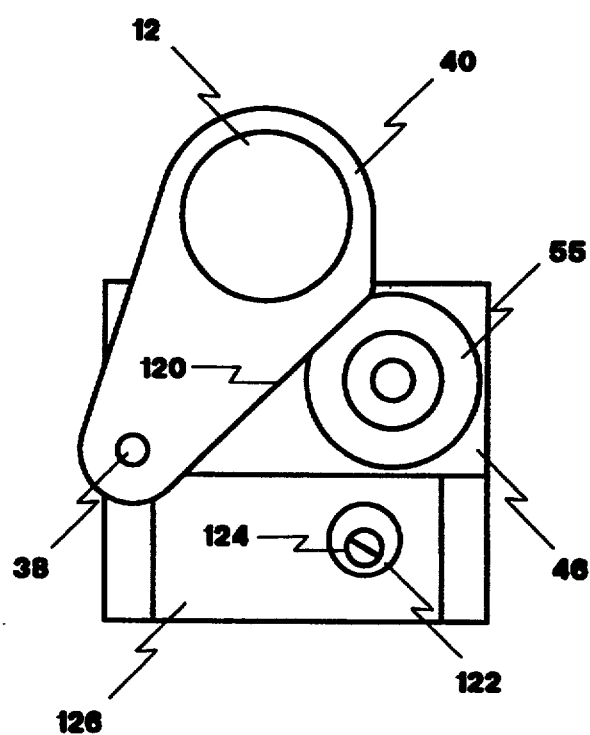
FIG. 8 is a side view of the receptor showing the focussing lens and its armature in a rest position.
Figure 9:
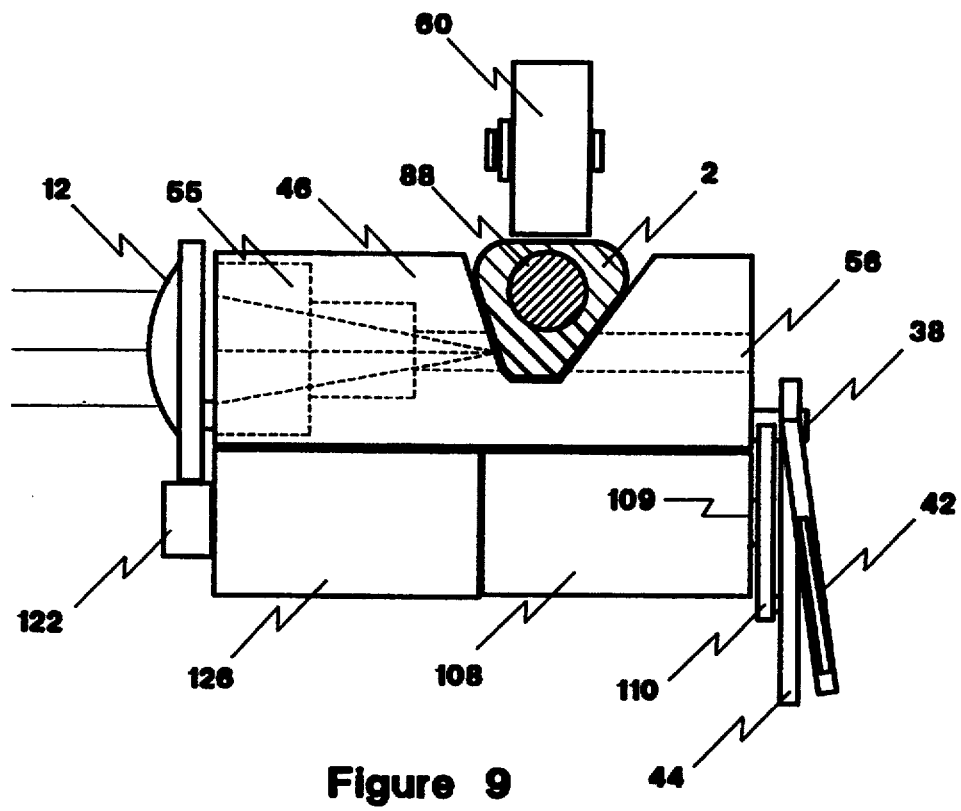
FIG. 9 is a front view of the device with a finger in the channel and the lens in position at the light path entrance to focus the light on the finger.
Figure 10:
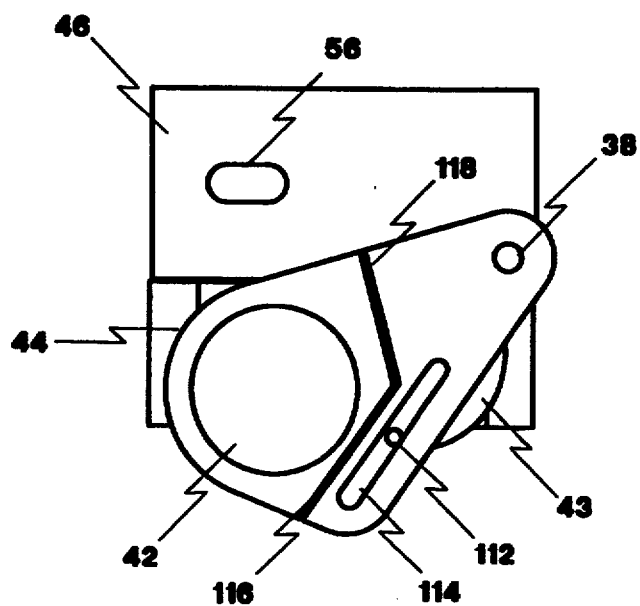
FIG. 10 is a side view showing the neutral density filter in a rest position.

In FIG. 6, it can be seen how the finger 2 is shaped by the base of the channel 48 to the shape of the channel so that a zone between the entrance 52 and the exit 54 and bounded by an inner surface 86 of the channel extending between said entrance and exit. In this manner, the path length from entrance to exit through the finger is constant for users having different sizes and shapes of fingers. Further, an outline of a typical finger bone 88 is shown and it can be seen that the bone is located above the light path extending through the finger from the entrance to the exit. The light can travel from the entrance 52 to the exit 54 through a fleshy part of the finger.

In FIGS. 7, 8, 9 and 10 the operation of the lens 12 and the neutral density filter 42 is shown in greater detail than was described in FIG. 1. The lens 12 is attached to the armature 40 which, in turn, is attached to a shaft 38. The shaft 38 extends through the base 46 parallel to the channel 48. At an end of the shaft 38 near the exit passage 56, the support 44 is affixed to the shaft 38. The neutral density filter 42 is mounted on the support 44. An electric motor 108 has a shaft 109 to which a positioning disk 110 is affixed. The positioning disk 110 contains a pin 112 that extends from a periphery of said disk 109 into a slot 114 of the support 44. The support 44 is cut along a line 116 and bent along a fold line 118 so that the neutral density filter 42 is mounted at an angle relative to the exit passage 56. In this manner, none of the light exiting from the exit passage 56 is reflected back into the passage by the filter 42. As the motor 108 turns the shaft 109, the disk 110 also turns and the pin 112 moves within the slot 114 to pivot the support 44 about a pivot point located on the shaft 38 to move the neutral density filter either from the position shown in FIG. 10 to a position where the filter is aligned with the exit passage 56 and vice-versa. As the support 44 rotates, the shaft 38 also rotates, which in turn causes the armature 40 to rotate about a pivot point on the shaft 38. When the armature 40 rotates, the lens 12 moves from the position shown in FIG. 8 to a position where the lens is aligned with the entrance passage 55. When that occurs, a lower edge 120 rests on an eccentrically mounted cam 122. The cam 122 is mounted on a shaft 124 of a scanning motor 126. When the lens is generally aligned with the entrance passage 55, the scanning motor 126 is activated to rotate the eccentric cam 122. This rotation causes the lens 12 to move constantly in a small circle relative to the entrance passage 55. Thus, when the finger is inserted in the channel 48 and the scanning motor 126 is activated, the lens will move continuously and will in turn move the light entering the entrance passage continuously relative to the finger.

The non-invasive monitoring device is based on the principle of measuring the absorbance of near-infrared radiation passing through some part of the body. According to the Beer-Lambert law, the concentration of constituents is proportional to a constant of proportionality (the extinction coefficient), the path length, and the absorbance (Log [l/T], where T is the transmittance i.e. the proportion of light of a given wavelength that is transmitted through the matrix). By measuring the absorbance at a number of predetermined wavelengths, some of which will control for path length, it is possible to calculate the concentration of a given constituent.

There are several ways in which this absorbance measurement may be taken and, without limiting the present invention, two methods are as follows: (1) Use the light from a scanning monochromator and pass it through a selected part of the body and collect the light transmitted through onto a silicon detector. A second measurement involves a measurement of the light transmitted in the absence of the body part. From these two measurements the transmittance, and hence the absorbance, may be calculated; (2) Use a polychromatic light source, pass it through the body part to be measured, collect the light, collimate it onto a diffraction grating and focus the different wavelengths of light on a linear array detector. Each element of the array will then measure the intensity of light for a narrow band of wavelengths. A similar measurement in the absence of the body part (reference scan) will then allow computation of the transmittance for each element. Because the various elements of the array have slightly different dark leakage currents, it is necessary to record a dark current and subtract it from both the sample scan and the reference scan before calculation of transmittance and absorbance.

In regard to absorbance measurement, a number of observations can be made.

Firstly, absorbtion of light for a specified constituent, at a particular wavelength, as already noted, is a function of the extinction coefficient for the constituent at that wavelength and the effective pathlength.

Secondly, the effective pathlength is determined by a combination of actual pathlength and scattering.

Thirdly, as wavelength increases, the extinction coefficients tend to increase, sometimes by orders of magnitude. The consequence of increasing extinction coefficients is that the effective pathlength must be decreased to compensate in order to keep absorbance measurements for standard instrumentation within a useable range (for example, 0.2–2.3 OD).

Fourthly, at wavelengths exceeding approximately 1600 nm, the extinction coefficient for water decreases optimal pathlength to about 1 mm in nonscattering media. Since most useful sites for in vivo measurement have tissue thicknesses exceeding 1 or 2 mm, absorbtion measurement in those cases and for these wavelengths is limited to reflectance measurement. It should be remembered that in reflectance measurement the tissue penetration depth is about one-half of the path length. This poses problems for use of the longer wavelengths as will be noted below.

The method of using a polychromatic light source described above is the preferred method because a single high speed scan of the array allows the user to collect data for all wavelengths at the same time. The monochromator only allows the user to collect data sequentially at a rate determined by the scan rate, the integration time of the detector, and the number of wavelength steps scanned. As an example, it takes a typical monochromator 500 msec to scan from 680 to 1150 nm. For a diode array, the scan of all elements (680 to 1150) can take 5 msec. If a pressure pulse ($\approx 100$ msec) from the heart causes the effective pathlength, and hence absorbance, to increase during the time of data acquisition all wavelengths are affected equally. For the monochromator, the pulse would selectively increase pathlength, and hence absorbance, for those wavelengths being measured during the occurrence of the pulse.

There are several parts of the body from which the measurements discussed here may be made. Included among these for transmission are: the finger, the lip, the ear lobe, a pinch of skin at the waist, the web between the thumb and forefinger. For reflectance, virtually any skin surface may be used. The question of adequate pathlength is important for both reflectance and transmittance. In the case of reflectance, some of the scattered light is eventually reflected back to the detector. In some cases, there may be one or more structures which have a highly reflective surface (e.g. the periosteum of the skull) which reflects the light back to the detector after covering a short path length. To measure significant changes in absorbtion, there must be sufficient pathlength through the tissues before the light is measured at the detector.

In a similar manner, for transmittance, the body part must have sufficient pathlength to produce useful absorbance values.

Regardless of the method used to measure absorbance, the detector has inherent limitations. In the wavelength region from 700 nm to 1200 nm, silicon detectors are typically used.

Performance of these detectors usually has been optimized for about 750 nm. This means that for a hypothetical light source with uniform intensity at all wavelengths, the peak output would be at 750 nm. For longer wavelengths in the region of 1100 nm, the response would drop off to about three percent of the response at 750 nm. For the shorter wavelengths, a similar reduction in response to about three percent would occur at 300 nm. The reduction in response at the upper and lower limits of the detector means that measurement of absorbance in these regions will be noiser, i.e., has increased error of measurement. Since in this application, absorbance needs to be measured at the longer wavelengths, it is necessary to average the results of several scans to get a better estimate of the absorbance.

Light entering the body is scattered and that light which emerges radiates in virtually every direction. This light scattering means that a limited proportion of the light can be captured by a lens system placed at the point where light exits from the body part. Further, the light that is captured for diffraction onto a diode array must be collimated and this further reduces the useful light available to the instrument. The result is that to measure the light falling onto a diode array it is necessary to integrate the light over a period of about 200 milliseconds. This period provides a useful amount of light for measuring the transmitted light. To prevent the array/detector from saturating during the reference scan it is necessary to place a neutral density filter in the path of the reference beam. Absorbance may be expressed in the usual manner, and by adding the constant OD of the neutral density filter at a given wavelength to the calculated absorbance it is possible to indicate the total effective optical density due to both absorbance and scattering.

There are several objectives in the design of a tissue interface:

(1) minimizing variability and maximizing repeatability of the readings;

(2) passing the light through the desired body tissue;

(3) optimizing pathlength and minimizing its variation between subjects; and (4) maximizing the throughput of light for the measurement.

Absorbtion begins at the point at which the light enters the tissue. In the case of transmission, as the light passes through the tissue, more and more light is absorbed as the path length increases. Clearly, if path length is too great, very little light is left for measurement and the absorbance calculations will be subject to considerable error due to noise.

The constitution of the tissue through which the light is directed determines the absorbtion of light at the measured wavelengths. Clearly, if the constituents to be measured are in the blood, it is preferable to pass the light through the capillary bed underlying the skin. For this same reason layers of fatty or connective tissue should be avoided to minimize absorbance in these tissues. The fingertip is thought to be the body part of choice for the foregoing reasons.

The shape of the entrance 52 is circular and a suggested size is 4 mm in diameter. At the exit, light is scattered almost evenly in every direction up to 60° from the optical path. Since the light is to be collimated, only that being emitted in line with the optical system is used so that the plane of the exit aperture is much less critical and may be placed at an angle between 45° and 90° to the optical center line. A suggested size for the exit 54 is 4 mm by 10 mm with the long side being parallel to the finger in order to increase the area from which light may be collected.

Under ideal positioning of the finger, the path length for various users will be constant. In practice, however, due to finger positioning, there will still be some variance in the path length for different users. To ensure that absorbance measurements are as consistant as possible, the receptor is designed to place the finger as consistantly as possible on repeated occasions in the same position for different individuals. This repeatability of placement in the receptor applies not only to the position along the length of the finger but also the location of the entry and exits in the channel on the lateral aspects of the finger. This repeatability of finger placement is best accomplished by providing a surface on which a palm of the hand may be rested while at the same time positioning the hand so that the middle finger may be inserted vertically into the receptor. When the finger is fully inserted into the channel, the roller will apply pressure over the first knuckle of the finger.

Even under ideal conditions, the path length will increase with each pressure pulse associated with each heart beat of the user.

Preferably, the hand is rested on a shelf that is at an angle of approximately 30° from the angle of the receptor. When the finger is inserted, a hood, preferably made of an opaque cloth, covers the hand and finger while measurements are being made.

A constant torsion spring is preferably used to maintain a constant pressure on the finger for fingers of different sizes. A leaf spring could also be used but the pressure applied to the finger will vary with the size of finger.

The combination of the roller pressing on the first knuckle of the finger and the shape of the channel tends to form the finger into the shape of the channel.

Averaging a number of measurements at a particular wavelength will minimize the noise and give a better estimate of the true "value" of the absorbance at the particular wavelength selected for averaging. The same averaging approach can be used to give a better estimate of the "true" finger absorbance for a particular wavelength by averaging out the effects of variability of finger placement and shaping. There are two approaches which may be used to perform this averaging.

One approach is to repeatedly place the finger into the light path, taking a measurement each time. This approach, of course, is time consuming and tiresome for the subject. The second approach involves some form of mechanical movement of the finger or light path which obviates the need to remove the finger from the instrument during measurement.

It is possible to move the subject's finger relative to the light path which would simulate repeated placements of the finger and permit averaging the results. It is important in this process that the positioning of the finger in the light path be accomplished in as nonsystematic a way as possible, otherwise there might be some systematic bias in the mean. Randomization of movement may be accomplished by randomly varying the period during which the finger is moved. There are two ways in which the finger may move in this way:

(a) Movements between measurements. This may be done by moving the finger, then scanning it to record an average absorbtion, moving it again, scanning again, and repeating this procedure as often as desired to obtain an averaged placement; and (b) It is also possible to continuously move and scan the finger, thus averaging both movement and scanning at the same time thereby reducing the time needed to acquire the necessary data. The danger of this approach is that synchronicity of scan and movement rate may bias the averaged results.

Since the movement of the finger in relation to the optical path is the same as movement of the optical path, the results of finger movement may also be achieved by moving the optical path, either wholly or in part. In fact, testing has shown that by simply making small movements using the single lens that focuses the light on the finger, it is possible to average finger position in a way equivalent to repeated placement of the finger.

The light path can be varied relative to the finger so that regardless of how the finger is positioned, the light path through the finger can be averaged to reduce the variability between repeated measurements. Preferably, the light path is varied by varying the point of focus of light entering the finger. Collimated light is directed onto a lens which focuses light onto the finger and the placement of the lens in the collimated beam is varied by an eccentric cam as measurements are made. The light, upon entering the finger is scattered. Some light is absorbed, some is scattered and reflected and the remainder is transmitted through the finger. Of that light transmitted through the finger, a portion is collected by the optical system, collimated, passed through a grating and focussed onto a linear array detector. Absorbance is calculated by expressing the light transmitted through the finger as a proportion of the light used to illuminate the finger.

When the finger is removed to permit measurement of the reference light intensity for callibration purposes, it is preferable to pass collimated light through the finger receptor. The second motor moves the scanning lens 12 out of the collimated light beam just prior to performing the reference measurement. The collimated beam passes through the entrance and exit of the receptor, which are aligned with the optical system. Since the light passing through the receptor has a much greater intensity when the finger is removed, it is necessary to position a neutral density filter in the path of the reference beam to prevent saturation of the linear array detector. This is accomplished by using the second motor so that the filter is placed in position just beyond the exit passage at the same time that the focussing lens is removed from the light path. Since the attenuation of the neutral density filter is a constant, measurement of absorbance may be expressed in relative terms or calculated by adding the constant to all absorbance readings.

Alternatively, a dual beam optical system can be used and, for the purpose of taking a reference measurement, part of the light can be reflected around the receptor by the same light collection system that is used with the receptor. Since only part of the light is reflected, the light intensity can be reduced by reducing the amount of light reflected and the neutral density filter can be eliminated.

What I claim as my invention is:

1. A finger receptor for use with a non-invasive monitoring device, said receptor being used with a light source to receive a finger of a user, said receptor comprising a base containing an elongated channel sized to receive a finger, said channel having an opening to receive said finger and two sides with a light path entrance on one side and a light path exit on another side, said entrance and exit being sized and located so that at least some of the light passing through said entrance is received at said exit, said channel being shaped so that a finger properly inserted into said channel completely fills a zone of said channel located between said entrance and exit so that no light from said entrance can reach said exit without passing through said finger, light from said light source forming an optical path from said entrance to said exit, with sensing means to determine when said finger is properly positioned in said channel.

2. A receptor as claimed in claim 1 wherein said zone is bounded by the entrance and exit and an inner surface of said channel extending between said entrance and said exit.

3. A receptor as claimed in claim 2 wherein there are means to reduce a level of intensity of said light source when a reference measurement is being taken using said monitoring device.

4. A receptor as claimed in claim 1 wherein the channel has a cross-sectional shape with a bottom that curves smoothly to a first side and a second side, said first side having said entrance located therein and being relatively steep, said second side having said exit located therein and having a gentle slope compared to said first side.

5. A receptor as claimed in claim 4 wherein there are means for moving the optical path relative to said finger as light from said light source is transmitted along said light path.

6. A receptor as claimed in claim 1 wherein there are pressure means to gently force the finger into an appropriate position when the finger is inserted into the channel, the pressure from said pressure means being of sufficient strength to slow blood flow in the finger but not to stop it and to concentrate blood adjacent to the entrance and exit.

7. A receptor as claimed in claim 5 wherein the means for moving the optical path relative to said finger is a movable lens mounted to the base in front of said light path entrance.

8. A receptor as claimed in claim 7 wherein said lens is mounted on an arm that is connected to a motor, said arm being movable and moving said lens relative to said finger when said monitoring device is in operation.

9. A receptor as claimed in claim 8 wherein there are means to reduce a level of intensity of said light source when a reference measurement is being taken using said monitoring device.

10. A receptor as claimed in claim 9 wherein the means to reduce the level of light intensity is a filter mounted between said light source and said monitoring device.

11. A receptor as claimed in claim 10 wherein the filter is mounted to the same arm as said lens but is offset from said lens so that the lens is located between said light source and said finger when the filter is not located to reduce the light intensity and the filter is located to reduce said light intensity from said receptor when said lens is not located between said light source and said finger.

12. A receptor as claimed in claim 1 wherein the sensing means is connected to automatically activate said monitoring device when said finger is properly positioned in said channel.

13. A receptor as claimed in claim 1 wherein there is a support connected to the receptor and located outside of said channel to support a hand of said user so that movement of the finger of said hand during operation of the monitoring device is minimized.

14. A receptor as claimed in claim 3 wherein the means to reduce the level of light intensity is a filter located within a path of said light.

15. A receptor as claimed in claim 3 wherein the means to reduce the level of light intensity are reflection means by which some of said light can be monitored.

16. A receptor as claimed in any one of claims 1, 2 or 3 wherein the channel is placed at an angle of approximately 30° from horizontal.

17. A receptor as claimed in claim 15 wherein the reflection means are a series of reflectors that reflect some of the light from the light source around said receptor so that the amount of light received by the monitoring device is reduced in intensity.

18. A receptor as claimed in any one of claims 1, 2 or 3 wherein there is a plunger slidably mounted in said channel, said plunger being spring-loaded and biased towards said opening so that said plunger is pushed away from said opening by said finger when said finger is inserted in said plunger triggering said sensor means when said finger is properly positioned in said opening.

19. A receptor as claimed in claim 6 wherein the pressure means is a roller rotatably mounted on a torsion spring-loaded armature that is biased toward said channel, said roller being located to contact said finger as it is being inserted and when the finger is located in the channel.

20. A receptor as claimed in claim 1 wherein the light entrance into said channel has a circular shape and the light exit from said channel has an oblong shape.

21. A receptor as claimed in claim 20 wherein the entrance converges through said base towards said channel and the exit has a constant size from said channel through said base.

22. A receptor as claimed in claim 21 wherein the entrance has side walls and converges in three steps, said side walls of the entrance being parallel to one another.

23. A receptor as claimed in any one of claims 1, 2 or 3 wherein the finger of the user has a finger bone and the channel is shaped so that the light path extending between the entrance and exit is located below the finger bone.

* * * * *

UNITED STATES PATENT AND TRADEMARK OFFICE
CERTIFICATE OF CORRECTION

PATENT NO. : 5,429,128

DATED : July 4, 1995

INVENTOR(S) : Theodore E. Cadell, et al.

It is certified that error appears in the above-identified patent and that said Letters Patent is hereby corrected as shown below:

ON THE TITLE PAGE

After item [22] please add:

--[30] Foreign Application Priority Data
    Aug. 29, 1990 [GB] Great Britain...................9018849.1
    Aug. 28, 1991     PCT     CA91/00305 --.

Signed and Sealed this

Fifteenth Day of July, 1997

Attest:

BRUCE LEHMAN

*Attesting Officer*       *Commissioner of Patents and Trademarks*